United States Patent
Gabriel et al.

(10) Patent No.: US 10,947,335 B2
(45) Date of Patent: Mar. 16, 2021

(54) TRIAZINE-PRECONDENSATE-ALDEHYDE CONDENSATION PRODUCTS AND METHOD FOR OBTAINING THE SAME

(71) Applicant: Borealis Agrolinz Melamine GmbH, Linz (AT)

(72) Inventors: Herbert Gabriel, Marienkirchen (AT); René Dicke, Leonding (AT); Helmut Puchinger, Freistadt (AT)

(73) Assignee: Borealis Agrolinz Melamine GmbH, Linz (AT)

( * ) Notice: Subject to any disclaimer, the term of this patent is extended or adjusted under 35 U.S.C. 154(b) by 80 days.

(21) Appl. No.: 16/308,671

(22) PCT Filed: Jun. 28, 2017

(86) PCT No.: PCT/EP2017/065940
§ 371 (c)(1),
(2) Date: Dec. 10, 2018

(87) PCT Pub. No.: WO2018/002106
PCT Pub. Date: Jan. 4, 2018

(65) Prior Publication Data
US 2019/0309119 A1 Oct. 10, 2019

(30) Foreign Application Priority Data
Jun. 29, 2016 (EP) ..................... 16176870

(51) Int. Cl.
| | | |
|---|---|---|
| *B27N 3/00* | (2006.01) | |
| *C08G 12/32* | (2006.01) | |
| *C09D 161/28* | (2006.01) | |
| *C07D 487/22* | (2006.01) | |
| *C07D 251/64* | (2006.01) | |
| *C09J 161/28* | (2006.01) | |

(52) U.S. Cl.
CPC .............. *C08G 12/32* (2013.01); *B27N 3/002* (2013.01); *C07D 251/64* (2013.01); *C07D 487/22* (2013.01); *C09D 161/28* (2013.01); *C09J 161/28* (2013.01)

(58) Field of Classification Search
CPC ...... C08G 12/32; B27N 3/002; C07D 251/64; C07D 487/22; C09D 161/28; C09J 161/28
USPC ......................................................... 528/254
See application file for complete search history.

(56) References Cited

U.S. PATENT DOCUMENTS

| | | | |
|---|---|---|---|
| 2,358,276 A | 9/1944 | Hodgins et al. | |
| 2,544,071 A | 3/1951 | Dudley et al. | |
| 3,250,708 A | 5/1966 | Dazzi et al. | |
| 3,372,131 A | 3/1968 | Rohlfs et al. | |
| 3,730,828 A | 5/1973 | Meiser | |
| 4,574,154 A | 3/1986 | Okamoto et al. | |
| 4,713,299 A | 12/1987 | Taylor et al. | |
| 5,216,156 A | 6/1993 | Galbo et al. | |
| 5,306,783 A | 4/1994 | Kirchgaessner et al. | |
| 5,330,846 A | 7/1994 | Eisele et al. | |
| 5,670,572 A | 9/1997 | Ott et al. | |
| 5,792,867 A | 8/1998 | Tanaka et al. | |
| 6,001,925 A | 12/1999 | Gapud et al. | |
| 6,077,614 A | 6/2000 | Conti et al. | |
| 6,307,046 B1 | 10/2001 | Tanaka et al. | |
| 6,458,748 B1 | 10/2002 | Yoshimura et al. | |
| 8,217,170 B2 | 7/2012 | Sala | |
| 8,802,848 B2 | 8/2014 | Dicke et al. | |
| 9,546,261 B2 | 1/2017 | Dicke et al. | |
| 2006/0051606 A1 | 3/2006 | Decher et al. | |
| 2006/0252909 A1 | 11/2006 | Pfeiffer et al. | |
| 2006/0276581 A1 | 12/2006 | Ratzsch et al. | |
| 2007/0172687 A1 | 7/2007 | Martin-Portugues et al. | |
| 2011/0105654 A1 | 5/2011 | Dicke et al. | |
| 2011/0178212 A1 | 7/2011 | Dicke et al. | |
| 2011/0230586 A1 | 9/2011 | Schwalm et al. | |
| 2012/0247559 A1 | 10/2012 | Nakamura et al. | |

FOREIGN PATENT DOCUMENTS

| | | |
|---|---|---|
| BE | 619876 A | 1/1963 |
| CA | 773096 A | 12/1967 |
| DE | 3700344 A1 | 4/1988 |
| DE | 3837965 A1 | 5/1990 |
| DE | 4129326 A1 | 3/1993 |
| DE | 4139961 A1 | 6/1993 |
| DE | 10301901 A1 | 7/2004 |
| DE | 102008016966 A1 | 10/2009 |
| EP | 0194080 A2 | 9/1986 |
| EP | 0268809 B1 | 9/1990 |
| EP | 0415371 A2 | 3/1991 |
| EP | 0710682 A2 | 5/1996 |
| EP | 0711760 A1 | 5/1996 |
| EP | 1057821 A1 | 12/2000 |

(Continued)

OTHER PUBLICATIONS 16308645 claims (Year: 2020).*
Santer, "Etherified Amino Resins: Synthesis and Reactions in Surface Coatings Applications", Progress in Organic Coatings, 1984, pp. 309-320, vol. 12, Elsevier Sequoia , Netherlands.

(Continued)

*Primary Examiner* — Irina S Zemel

(74) *Attorney, Agent, or Firm* — The Webb Law Firm

(57) ABSTRACT

The present invention relates to a triazine-precondensate-aldehyde condensation product obtainable by reacting a) at least one triazine compound of the general formulae (I), b) at least one aldehyde, and c) at least one triazine precondensate of the general formula (II). A method for obtaining a condensation product and a wood based panel are also disclosed.

19 Claims, 1 Drawing Sheet

(56) References Cited

FOREIGN PATENT DOCUMENTS

| EP | 1247837 | B1 | 5/2008 |
|---|---|---|---|
| EP | 2332926 | A1 | 6/2011 |
| EP | 2743282 | A | 6/2014 |
| JP | 200063360 | A | 2/2000 |
| JP | 2004268500 | A | 9/2004 |
| JP | 2006231768 | A | 9/2006 |
| JP | 200856866 | A | 3/2008 |
| RU | 2337928 | C2 | 11/2008 |
| RU | 2014113461 | A | 12/2015 |
| SU | 66303 | A1 | 11/1945 |
| WO | 9630422 | A1 | 10/1996 |
| WO | 9802474 | A1 | 1/1998 |
| WO | 2005118718 | A1 | 12/2005 |
| WO | 2007012617 | A1 | 2/2007 |
| WO | 2008061923 | A1 | 5/2008 |
| WO | 2009121603 | A1 | 10/2009 |
| WO | 2009121607 | A1 | 10/2009 |
| WO | 2011015539 | A1 | 2/2011 |
| WO | 2013041592 | A1 | 3/2013 |

OTHER PUBLICATIONS

Shechter et al., "Glycidyl Ether Reactions with Amines", Industrial and Engineering Chemistry, Jan. 1956, pp. 94-97, vol. 48, No. 1.

Shinoda et al., "Shape-selective N-alkylation of melamine using alcohol as an alkylating agent with Ru/mordenite catalyst in the liquid phase", Studies in Surface Science and Catalysis, 2000, pp. 3465-3470, vol. 130, Elsevier Science B.V.

Patel, R. et al., "Facile Synthesis, Characterization and Properties of Triazine Based Dendrimer", International Journal of Chemical Science, 2014, pp. 353-365, vol. 12(2), Sadguru Publications, Udaipur, India.

Xiuxiu, L. et al, "Facile Synthesis of Dendritic Hydroxyl-terminated Cyanuric Chloride Derivatives and Their Properties", Chinese Journal of Chemistry, 2012, pp. 1485-1489, vol. 30(7), SIOC, CAS, Shanghai & Wiley-VCH Berlag GmbH & Co. KGaA, Weinheim.

Beyer et al., "Über Methacryloyl-bzw. Acryloyl-dicyandiamid und einige s-Triazin-Derivate", Chemische Berichte, 1966, pp. 2123-2126, vol. 99, (English-language Abstract).

Kreutzberger, "Reactions of Trichloromethyl-1,3,5-triazine Derivatives with Amines", Journal of the American Chemical Society, 1957, pp. 2629-2633, vol. 79, No. 10.

* cited by examiner

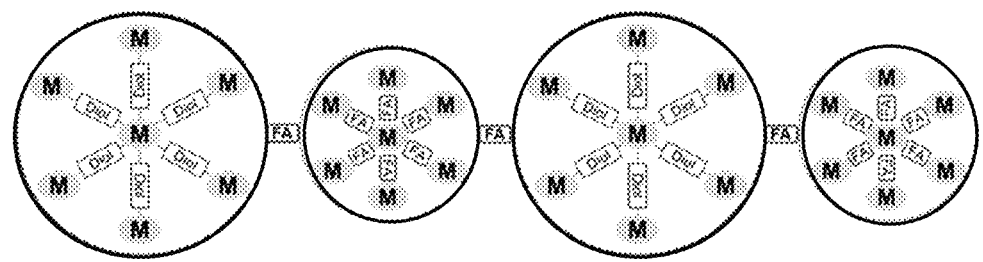

TRIAZINE-PRECONDENSATE-ALDEHYDE CONDENSATION PRODUCTS AND METHOD FOR OBTAINING THE SAME

CROSS-REFERENCE TO RELATED APPLICATIONS

This application is the United States national phase of International Application No. PCT/EP2017/065940 filed Jun. 28, 2017, and claims priority to European Patent Application Number 16176870.0 filed Jun. 29, 2016, the disclosures of which are hereby incorporated in their entirety by reference.

BACKGROUND OF THE INVENTION

Field of the Invention

The present invention relates to triazine-precondensate-aldehyde condensation products, a method for obtaining the same, use of the condensation product and wood based panels comprising the same.

Melamine is an important raw material in the production of resins for the manufacture of laminates for surface finishing, moulding compounds, paints and glues. Melamine-formaldehyde-resins as products of a condensation of melamine and formaldehyde are characterized by exceptional hardness, high gloss, flame retarded, as well as heat and solvent resistance.

Description of Related Art

Melamine formaldehyde resins are mainly used in the wood industry as adhesives in wood panels, as impregnation resin in laminates, as linking agents or as composite material. These conventional resins are highly linked and provide therefore stiff and hard duroplastic materials. An unmodified melamine formaldehyde resin forms a dense network during the condensation. The degree of crosslinking depends thereby on different factors such as the melamine/formaldehyde ratio, temperature and pH-value.

Since melamine-formaldehyde resins are stiff, brittle and have a reduced flexibility they often cause problems in the processabilty and postforming or dimensional stability properties of laminates and other melamine-formaldehyde resin containing products. Due to the low flexibility the laminate may crack for instance when bending the laminate over the edge. The smaller the radius the more difficult is the post-forming process. As mentioned a high brittleness of the resin may causes problems in processing. For instance, cutting tools are of limited life time due to the exposure by the hard surface and also the edges of the laminate surface can shatter or splinter during processing.

Different methods are known in order to circumvent these problems. For instance, a common way to increase the flexibility of a thermoset material is on the one hand to add plasticisers with a reduced functionality compared to melamine. Another approach for increasing flexibility and to reduce the degree of linkage is reducing the ratio of formaldehyde to melamine. This method is however hampered by reduced stability and solubility problems of the aqueous resin.

Besides the low flexibility of conventional melamine-formaldehyde resins the content of the carcinogenic formaldehyde in such resins is relative high. Several attempts have been made in the past to reduce the formaldehyde concentration. For example suitable aldehyde scavengers are added to the formaldehyde resin. However, a mere reduction of formaldehyde may not be sufficient in the future in order to oblige to tighter regulations.

Thus, it would be of an advantage to provide a triazine resin that combines a high flexibility with a reduced formaldehyde content.

SUMMARY OF THE INVENTION

It was thus an object of the present invention to provide novel triazine resins that are based on triazine units, in particular melamine, but show a reduced amount of formaldehyde and have at the same time thermoplastic properties.

This object is being solved by a triazine-precondensate-aldehyde condensation product as described herein and a method for obtaining the same.

Accordingly, a triazine-precondensate-aldehyde condensation products is provided that is obtainable by reacting a) at least one triazine compound of the general formulae (I)

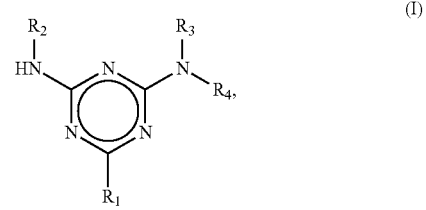

b) at least one aldehyde, in particular formaldehyde, and
c) at least one triazine precondensate of the general formula (II)

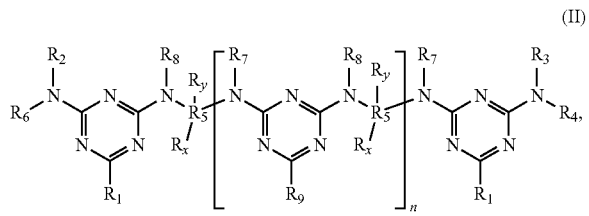

wherein $R_1$ means $Q^1$ or a moiety of the formula $R_3$—N—$R_4$ connected with the nitrogen atom to the respective triazine ring of the structure of formula (I) or (II), $R_9$ means $Q^1$ or a moiety of the formula $R_7$—N—$R_8$ connected with the nitrogen atom to the triazine ring of the structure of formula (I), $R_2$, $R_3$, $R_4$ and $R_6$ mean independently from each other H, $Q^1$ or

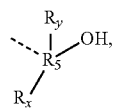

$R_7$ and $R_8$ mean independently from each other H, $Q^1$,

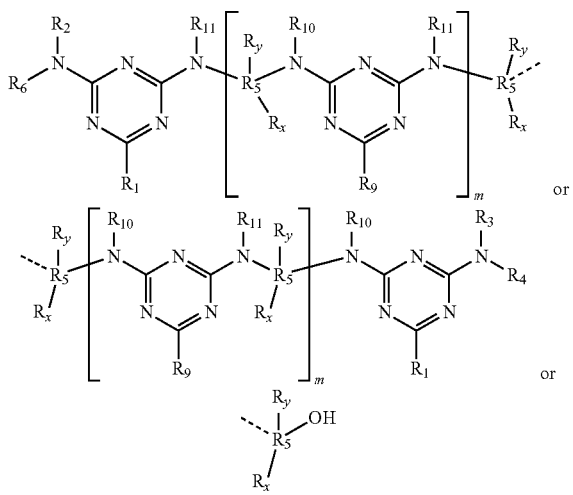

$R_{10}$ and $R_{11}$ mean independently from each other $R_7$ or $R_8$;

$R_5$ means linear or branched $C_2$-$C_{20}$-alkyl that can be interrupted by one or more oxygen atoms, sulphur atoms, substituted or non-substituted nitrogen atoms.

$R_x$, $R_y$ mean independently from each other H, OH, $Q^1$, —[$C_1$-$C_{18}$]—OH or

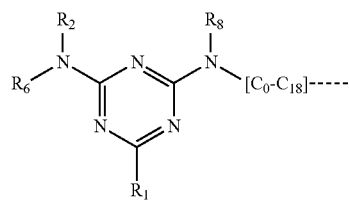

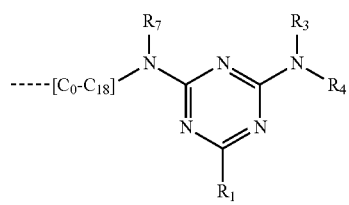

wherein $Q^1$ means linear or branched $C_1$-$C_{20}$-alkyl, linear or branched $C_2$-$C_{20}$-alkenyl, linear or branched $C_2$-$C_{20}$-alkinyl, $C_3$-$C_{10}$-cycloalkyl, $C_5$-$C_7$-cycloalkenyl, which in each case can be interrupted by one or more oxygen atoms, sulphur atoms, substituted or non-substituted nitrogen atoms and/or by one or more groups of the type —C(O)O—, —OC(O)—, —C(O)—, —NHC(O)O—, —OC(O)NH— and/or —OC(O)O—; and wherein n=0-10, preferably 1-8, most preferably 1-5, m=0-8, preferably 1-7, most preferably 1-5, or mixtures thereof.

Thus, a condensation product is provided, wherein multiple triazine units are preferably connected to each other via longer alkyl linkers or alkyl bridges, and via alkylene bridges, such as methylene bridges. That means that methylene bridges are present in the condensation product only in a limited amount. The number of possible methylene bridges can be adjusted by the amount of aldehyde, in particular formaldehyde, added to the reaction mixture.

Furthermore, due to the longer alkyl bridges or alkyl linkers a condensation product with increased flexibility and thus reduced brittleness compared to conventional melamine-formaldehyde resins is provided.

The condensation product of the present invention may also be schematically described in the following manner (see scheme in FIG. 1).

The triazine precondensate of formula (II) such as a melamine-diol-precondensate react with a triazine of general formula (I) and an aldehyde, in particular formaldehyde. This reaction provides a condensation product zones of the melamine-diol-precondensate (big circles) and melamine-formaldehyde-condensate (small circles). Both zones (or circles) are linked to each other by formaldehyde. The melamine-diol-precondensate zone can be seen as flexible soft unit that is linked to the rather non-flexible hard melamine-formaldehyde-condensate thereby forming an overall rather flexible rubber-like condensation product.

In a preferred embodiment of the present condensation product the at least one triazine of general formulae (I) is selected from a group comprising melamine, acetoguanamine, benzoguanamine or alkylated melamine. Melamine is however the preferred triazine of general formulae (I).

It is in general also conceivable to add (besides the at least one triazine) at least one further amino compound, in particular urea or a derivative thereof. In case urea is added as additional compound a triazine-urea-precondensate-aldehyde condensation product is obtained.

In a yet further preferred embodiment of the present condensation product the at least one aldehyde used is formaldehyde. However, the use of other aldehydes such as acetaldehyde, glyoxal or dimethoxyethanal may also be suitable.

The molar ratio of the at least one triazine of general formulae (I) and the at least one precondensate of the general formulae (II) is in a range between 100:1 and 1:100, preferably in a range between 50:1 and 1:50, most preferably between 30:1 and 1:30. A molar excess of the triazine of general formulae (I) in respect to the precondensate of general formulae (II) is however preferred.

The molar ratio of the at least one aldehyde such as formaldehyde to the at least one triazine of general formulae (I) is in a range between 0.4:1 and 3:1, preferably between 0.8:1 and 2:1, most preferably between 1:1 and 1.5:1.

The molar ratio of the at least one aldehyde to the at least one triazine precondensate of general formulae (II) is in a range between 0.4:1 and 3:1, preferably between 0.8:1 and 2:1, most preferably between 1:1 and 1.5:1.

The present condensate has preferably an average molar mass $M_w$ between 400 and 5000 g/mol, preferably between 500 and 3000 g/mol.

Furthermore, the storage stability of the present condensate may be between 1 and 40 days, preferably between 3 and 30 days, most preferably between 5 and 20 days. In general, a long storage stability is preferred.

In an embodiment the moiety $Q^1$ is a linear or branched $C_1$-$C_{12}$-alkyl, $C_3$-$C_7$-cycloalkyl and linear or branched $C_2$-$C_{12}$-alkenyl.

In a further embodiment the moiety $Q^1$ is a linear or branched $C_1$-$C_6$ alkyl, preferably a $C_2$, $C_3$ or $C_4$ alkyl. $Q^1$ can be for example a methyl, ethyl, n-propyl, isopropyl, n-butyl, s-butyl, t-butyl, isobutyl, pentyl, cyclopentyl, hexyl, cyclohexyl, 2-ethyl-hexyl, octyl, decyl, stearyl, phenyl, toloyl, xyloyl, hydroxyethyl, hydroxypropyl or hydroxybutyl.

In an embodiment the moiety $R_5$ is a linear or branched $C_2$-$C_{20}$ alkyl, preferably a linear or branched $C_2$-$C_{10}$ alkyl, more preferably a linear or branched $C_3$-$C_5$ alkyl.

It is furthermore preferred if the moieties $R_x$, $R_y$ are H, OH, linear or branched $C_1$-$C_{10}$ alkyl, preferably linear or branched $C_2$-$C_6$, or linear or branched [$C_1$-$C_{10}$]—OH, preferably linear or branched [$C_2$-$C_6$]—OH.

In a preferred embodiment the moieties $R_2$, $R_3$, $R_4$, $R_6$, $R_7$ and $R_8$ are a $C_1$-$C_6$ alkyl comprising in one or more cases at least one OH substituent, in particular a hydroxybutyl.

In a most preferred embodiment the moieties $R_2$, $R_3$, $R_4$, $R_6$, $R_7$ and $R_8$ are in each case H and $R_5$ is a $C_2$-$C_6$ alkyl, in particular non-substituted —$C_2H_4$—, —$C_3H_6$—, —$C_4H_8$—, —$O_5H_{10}$— or —$C_6H_{12}$-moiety.

In yet a further variant the precondensate of general formulae (II) comprises two, three or four triazine rings wherein at least one of the moieties $R_2$, $R_3$, $R_4$, $R_6$, $R_7$ and $R_8$ is a $C_2$-$C_6$ alkyl, in particular a $C_4$-$C_6$ alkyl moiety comprising in one or more cases at least one OH substituent or a double bond.

It is also possible that a precondensate of general formulae (II) of two or three triazine rings may comprise only one of the moieties $R_2$, $R_3$, $R_4$, $R_6$, $R_7$ and $R_8$ that are not H. Thus, the alkyl moiety (i.e. $R_2$, $R_3$, $R_4$, $R_6$), in particular a $C_4$-$C_6$ alkyl moiety, preferably with an OH substituent, can be arranged as a terminal moiety on the triazine ring or the alkyl moiety (i.e. $R_7$ and $R_8$) is provided as an internal moiety within the precondensate of general formulae (II).

In it is also conceivable that some of the moieties will undergo a cyclization reaction. For example, moieties $R_2$ and $R_6$ or $R_3$ and $R_4$ can form a cycloalkyl or heterocycloalkyl ring, respectively. It is also conceivable that moieties $R_7$ and $R_8$ may undergo a cyclization reaction with one of the moieties $R_x$ and $R_y$. It is to be understood that any cyclization reaction depends on the chain length of any of said moieties and possible further substituents enabling ring cyclization such as OH or $NH_2$-moieties.

In case the moieties $R_2$ and $R_6$ and/or $R_3$ and $R_4$ form a cycloylalkyl or heterocycloalkyl ring said ring may be a $C_5$-$C_6$-cycloalkyl, pyrrolidin, morpholine, tetrahydrofuran, piperidin, tetrahydropyran that may be further substituted.

The moieties, in particular Q1 and $R_5$, can be further substituted. Here the term "substituted", in particular in connection to alkyl, alkenyl, alkinyl, cycloalkyl, cycloalkenyl relates to the substitution of one or more atoms, usually H-atoms, by one or more of the following substituents: halogen, hydroxy, protected hydroxy, oxo, protected oxo, $C_3$-$C_7$-cycloalkyl, phenyl, naphthyl, amino, protected amino, primary or secondary amino, heterocyclic ring, imidazolyl, indolyl, pyrrolidinyl, $C_1$-$C_{12}$-alkoxy, $C_1$-$C_{12}$-acyl, $C_1$-$C_{12}$-acyloxy, nitro, carboxy, carbamoyl, carboxamid, N—($C_1$-$C_{12}$-alkyl)carboxamid, N,N-Di($C_1$-$C_{12}$-alkyl)carboxamid, cyano, methylsulfonylamino, thiol, $C_1$-$C_{10}$-alkylthio and $C_1$-$C_{10}$-alkylsulfonyl. The substituted groups can be once or twice substituted with same or different substituents.

Examples for the above substituted alkyl groups comprise 2-oxo-prop-1-yl, 3-oxo-but-1-yl, cyanomethyl, nitromethyl, chlormethyl, hydroxymethyl, tetrahydropyranyloxymethy, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chlormethyl, brommethyl, iodmethyl, trifluormethyl, 6-hydroxyhexyl, 2,4-dichlor(n-butyl), 2-aminopropyl, 1-chlorethyl, 2-chlorethyl, 1-bromethyl, 2-bromethyl, 1-fluorethyl, 2-fluorethyl, 1-iodethyl, 2-iodethyl, 1-chlorpropyl, 2-chlorpropyl, 3-chlorpropyl, 1-brompropyl, 2-brompropyl, 3-brompropyl, 1-fluorpropyl, 2-fluorptopyl, 3-fluorpropyl, 1-iodpropyl, 2-iodpropyl, 3-iodpropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and alike.

Examples for the above substituted alkenyl groups comprise styrolyl, 3-chlor-propen-1-yl, 3-chlor-buten-1-yl, 3-methoxy-propen-2-yl, 3-phenyl-buten-2-yl, 1-cyano-buten-3-yl and alike.

The term "alkinyl" as used herein relates to a moiety of the formulae R—C≡C—, in particular to a $C_2$-$C_{50}$-Alkinyl". Examples for $C_2$-$C_{50}$-alkinyle comprise ethinyl, propinyl, 2-butinyl, 2-pentinyl, 3-pentinyl, 2-hexinyl, 3-hexinyl, 4-hexinyl, 2-heptinyl, 3-heptinyl, 4-heptinyl, 5-heptinyl, octinyl, noninyl, decinyl, undecinyl, dodecinyl, as well as di- and tri-ines of straight or branched alky chains.

The term "$C_1$-$C_{12}$-alkyl" relates to moieties like methyl, ethyl, n-propyl, isopropyl, n-butyl, isobutyl, s-butyl, t-butyl, amyl, t-amyl, hexyl, heptyl, octyl, nonyl, decyl, undecyl, dodecyl, and alike. Prefererd $C_1$-$C_{12}$-alkyl groups are methyl, ethyl, isobutyl, s-butyl und isopropyl.

The term "oxo" relates to a carbon atom, which is connected with an oxygen atom via a double bond whereby a keto or an aldehyde group is formed. The term "protected oxo" relates to a carbon atom, which is substituted by two alkoxy groups or is connected twice with a substituted diol forming a non-cyclic or cyclic ketal group.

The term "alkoxy" relates to moieties like methoxy, ethoxy, n-propoxy, isopropoxy, n-butoxy, t-butoxy and alike. A preferred alkoxy group is methoxy.

The term "$C_3$-$C_7$-cycloalkyl" comprises groups like cyclopropyl, cyclobutyl, cyclopentyl, cyclohexyl und cycloheptyl. The term "$C_5$-$C_7$-Cycloalkenyl" relates to a 1,2 oder 3-cyclopentenyl ring, a 1,2,3 or 4-cyclohexenyl ring or a 1,2,3,4 or 5-cycloheptenylring.

In a preferred embodiment of the present invention the precondensate of the general formulae (II) may have one of the following structures:

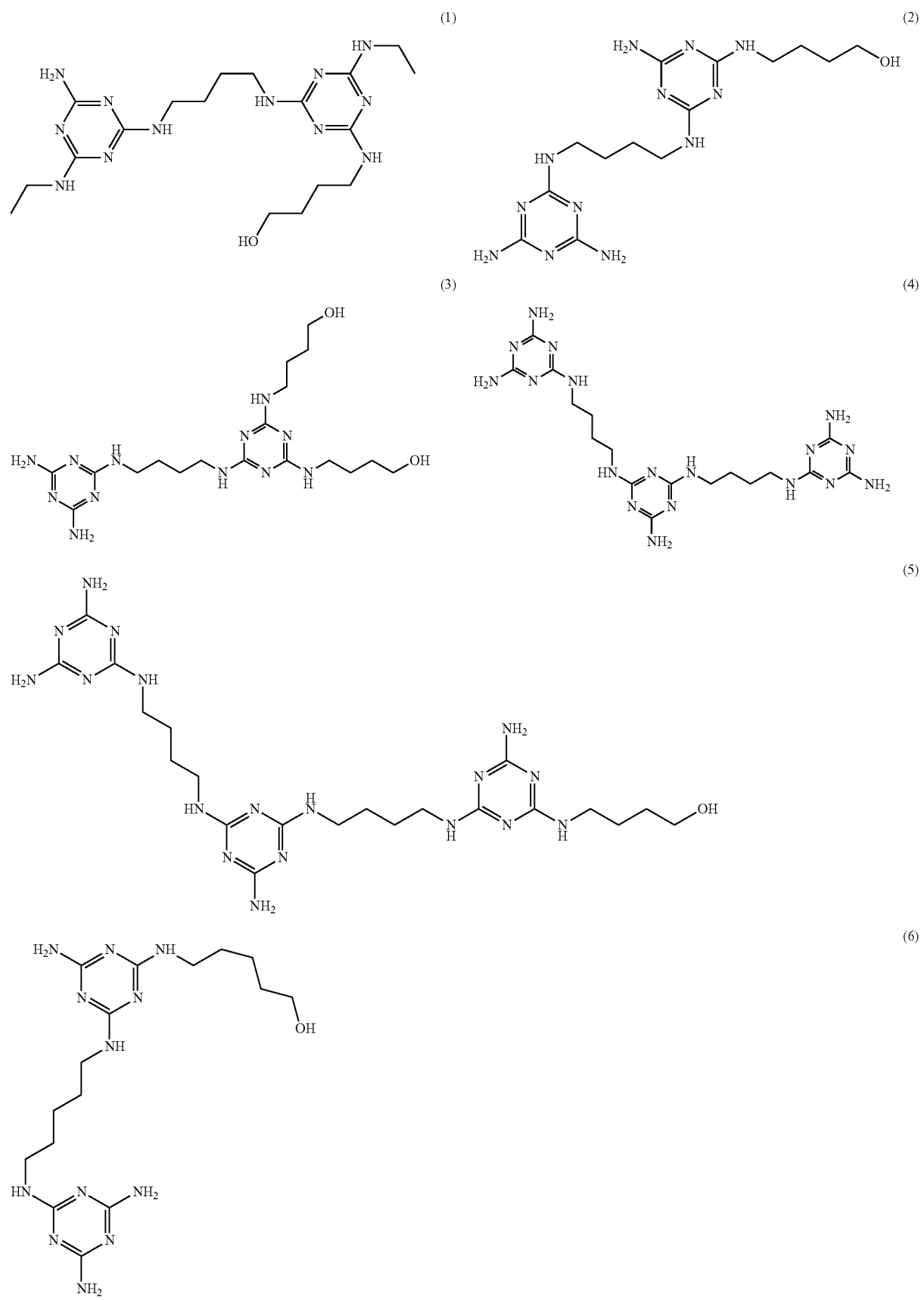

-continued
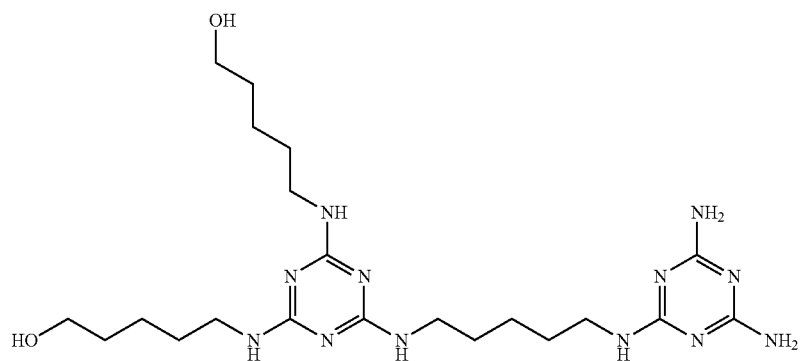
(7)
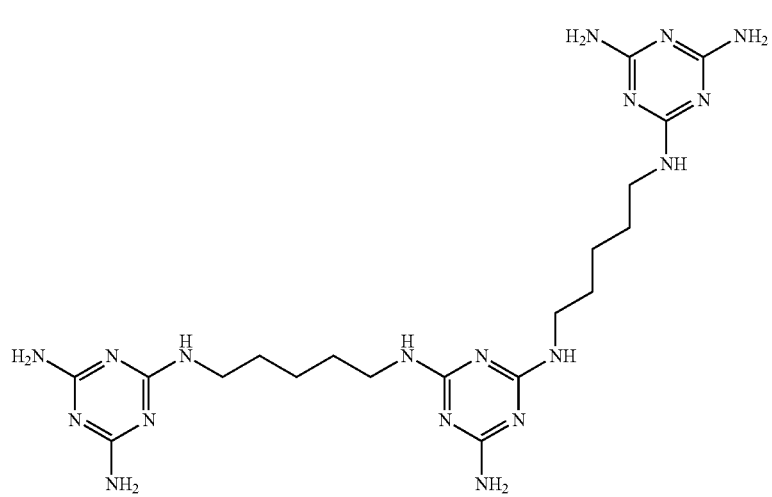
(8)
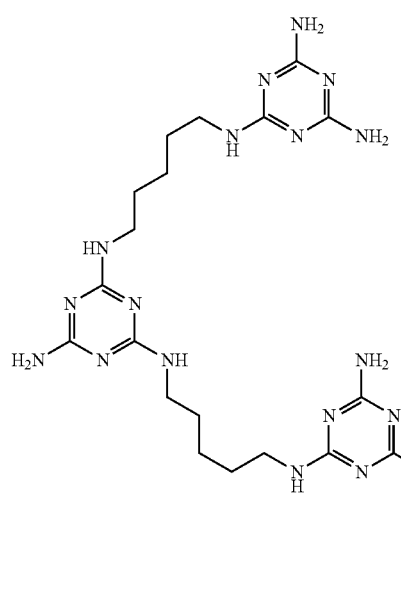
(9)
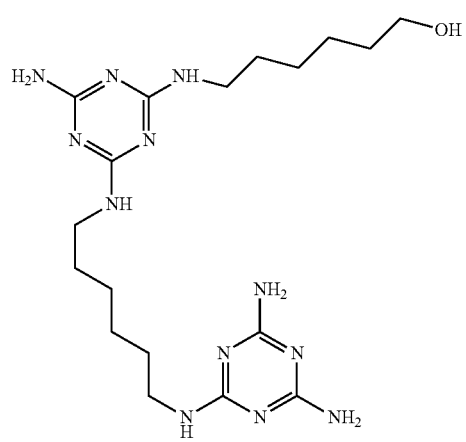
(10)

-continued
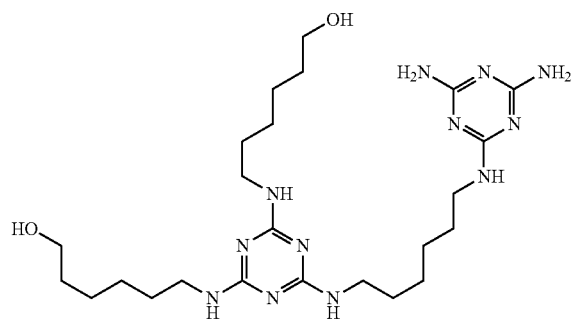
(11)
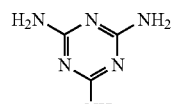
(12)
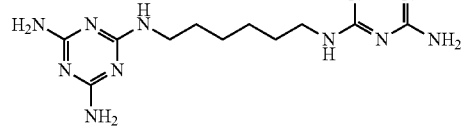
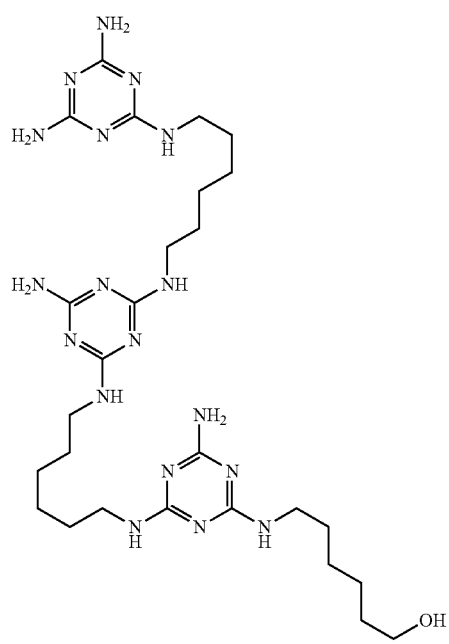
(13)
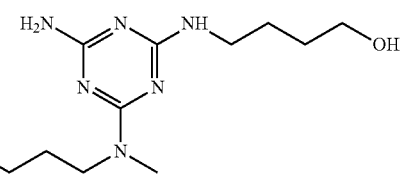
(14)
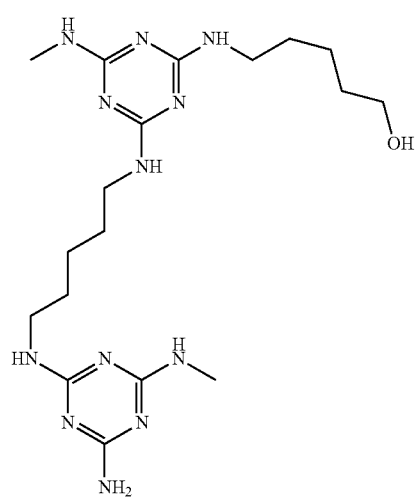
(15)
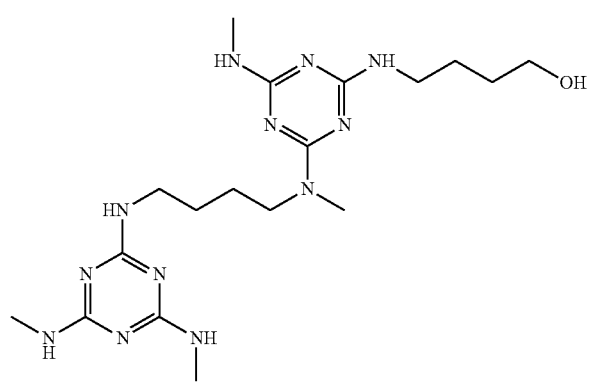
(16)

The triazine precondensate of general formulae (II) is obtained in a method, wherein
at least one triazine of the general formula (III)

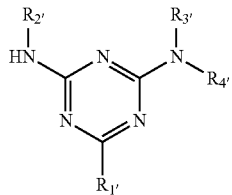

and at least one alcohol of the general formula (IV)

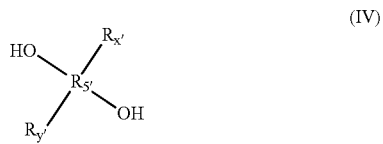

or a mixture of at least one alcohol of general formula (IV) and general formula (V)

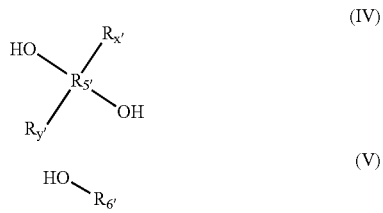

wherein $R_1'$, $R_2'$, $R_3'$, $R_4'$, $R_5'$, $R_6'$, $R_x'$ and $R_y'$ have the meanings of $R_1$, $R_2$, $R_3$, $R_4$, $R_5$, $R_6$, $R_x$ and $R_y$,
are reacted.

The moiety $R_5'$ in the alcohol of general formula (IV) may be linear or branched $C_2$-$C_{20}$ alkyl, preferably a linear or branched $C_2$-$C_{10}$ alkyl, more preferably a linear or branched $C_3$-$C_6$ alkyl. Thus, alcohol according to general formula (IV) can be selected from a group comprising diols, in particular ethandiol, propandiol, butandiol, pentandiol or hexandiol, diethylenglycol, triethanolamine, diethanolamine, triols (such as trimethylol propane) and tetraols (such as pentaerythrit). The alcohol according to general formula (V) can be any suitable monoalcohol.

The triazine of formula (III) may be preferably selected from a group comprising melamine, acetoguanamine, benzoguanamine or alkylated melamine. Melamine is however the preferred triazine of general formulae (III).

The reaction of triazine of general formulae (III) and alcohol(s) is carried out in the presence of one catalyst selected from a group comprising a metal or metal oxide, wherein the metal is from 8th, 9th or 10th group of the periodic system, wherein the one catalyst does not comprise any carrier material. Thus, only one metal, metal oxide, metal salt or metal complex catalyst is used that is free of any type of carrier material. Furthermore, no binary catalytic system such as a mixture of two catalysts is used. In a preferred embodiment the one catalyst does not comprise any acidic carrier material, in particular no zeolithe, alumo silicate, alumo phosphate, metal oxide, silicate, layered silicate, aluminium oxide, silizium dioxide and/or carbon. In an embodiment the catalyst comprises a metal or metal oxide selected from a group comprising Ru, Rh, Pd, Pt, Co, Fe. In particular a preferred catalyst is selected from the group comprising triruthenium dodecarbonyl, Potassium perruthenate $KRuO_4$, Ruthenium(III) acetylacetonate $(C_5H_7O_2)_3Ru$, Ruthenium(IV) oxide $RuO_2$ sowie Palladium (II) oxide PdO, Hexaamineruthenium(III) chloride [Ru$(NH_3)_6$]$Cl_3$, ruthenium(III) nitrosylchloride $Cl_3NORu$, potassium pentachloronitrosylruthenium(II), tetraacetatochlorodiruthenium(II,III), dichlorobis(2,2'-bipyridyl)ruthenium(II), tris(2,2'-bipyridyl)ruthenium(II) chloride, Rhodium(III) nitrate hydrate $Rh(NO_3)_3.xH_2O$, Rhodium(III) chloride $RhCl_3$, Palladium(II)acetate $C_4H_6O_4Pd$, Palladium(II)acetonylacetate $C_{10}H_{14}O_4Pd$, Palladium(II)chloride $PdCl_2$, Platinum (IV)chloride $PtCl_4$, Platinum(II)chloride $PtCl_2$, Platinum(IV)oxide $PtO_2$, Potassium hexachloroplatinate(IV) $Cl_6K_2Pt$, Sodium hexahydroxyplatinate(IV) $H_6Na_2O_6Pt$, Tetraamineplatinum(II) chloride hydrate $H_{12}Cl_2N_4Pt.xH_2O$, Cobalt(II) acetylacetonate $C_{10}H_{14}CoO_4$, Sodium hexanitrocobaltate(III) $CoN_6Na_3O_{12}$, Cobalt carbonyl $CO_2(CO)_8$, Diironnonacarbonyl $Fe_2(CO)_9$, Iron(III) acetylacetonate $C_{15}H_{21}FeO_6$, Triirondodecacarbonyl $Fe_3(CO)_{12}$, Potassium ferrate(VI) $K_2FeO_4$.

The amount of catalyst required may be between 0.001 to 2 Mass %, preferably 0.01 to 1.5 Mass %, mostly preferably 0.1 to 1 Mass % in respect to the triazine, in particular melamine.

In a further embodiment of the present method the reaction is carried out at a temperature between 80° C. and 300° C., in particular 150° C. and 270° C., in particular 180° C. and 260° C.

In yet another preferred embodiment of the present method the reaction time is at least 2 hours, preferably at least 6 hours. Specifically the reaction time is between 4 and 12 hours, preferably between 5 and 10 hours, most preferably between 6 and 8 hours.

In a mostly preferred embodiment the molar ratio of the at least one triazine of the general formula (III) and the at least one alcohol of the general formula (IV) or the mixture of the at least one alcohol of the general formula (IV) and at least one alcohol of the general formula (V) is between 1:0.3 to 1:3, preferably 1:0.5 to 1:2, mostly preferably 1:0.6 to 1:1.6.

When using a mixture of the alcohol of formula (IV) and an alcohol of formula (V) as reaction partner for the triazine of formula (III) the ratio of alcohol of formula (IV) and alcohol of formula (V) may be between 1:0 to 1:2, preferably 1:0 to 1:1.5, most preferably 1:0 to 1:0.8.

A ratio close to equimolar of triazine and alcohol is particularly preferred. When using an equimolar ratio of triazine and alcohol not all amino groups on the triazine ring will react with the alcohol. Thus, the triazine molecules are forced to undergo a reaction with each other thereby forming dimers, trimers and higher oligomers.

The reaction is carried out in a pressure range between 1 bar and 100 bar, preferably between 5 bar and 50 bar. The reaction may be started under normal pressure or also at higher pressure of about 5 bar. It is to be understood that the pressure may increase in the course of the reaction in conjunction with a temperature increase.

The reaction of the at least one triazine according to general formulae (III) and any of the alcohols of general formulae (IV) and (V) may be carried out in a hydrogen gas atmosphere, preferably in a mixture of hydrogen gas and an inert gas such as nitrogen, argon or helium.

The precondensate reaction is carried out under normal pressure, preferably in a hydrogen gas atmosphere. Thus, a pressure of about 1 bar (0.1 MPa) prevails in the reaction vessel or chamber.

An example of a precondensation reaction providing a triazine precondensate of general formulae (II) is shown in the following reaction scheme:

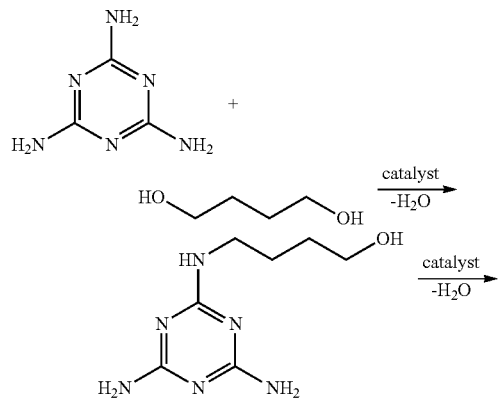

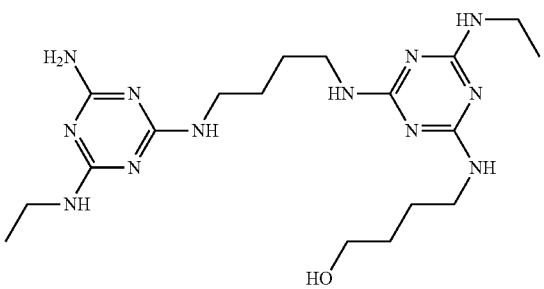

In one embodiment the present triazine-precondensate-aldehyde condensation product (17) with a molar mass of about 2500 g/mol can be obtained from melamine (as triazine of general formulae I), formaldehyde and a precondensate of general formulae (II) that in turned was obtained from the reaction of melamine and butanediol:

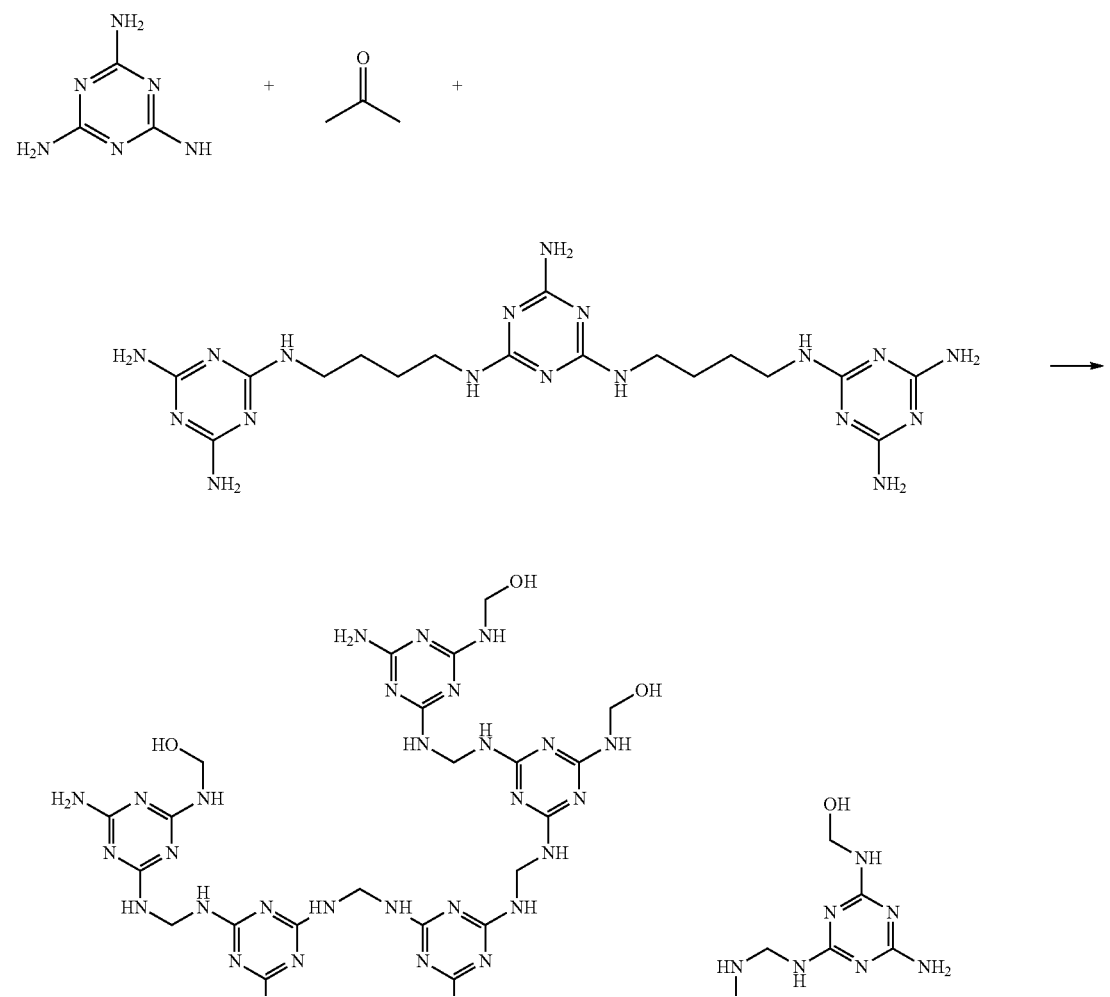

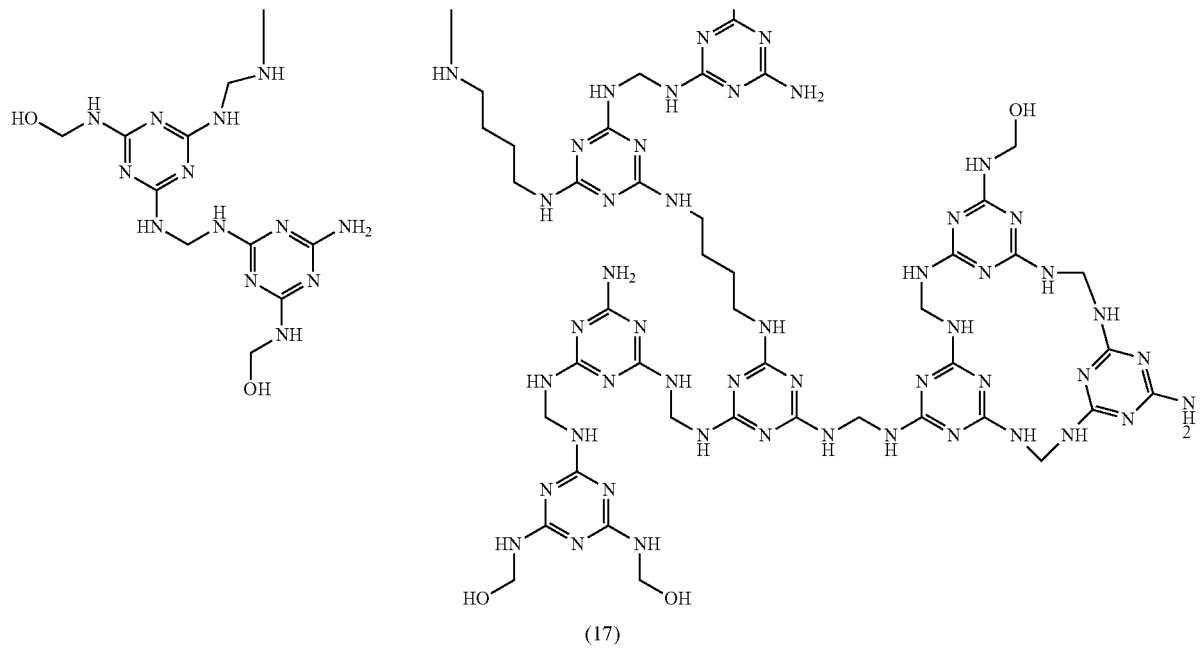

(17)

The above structure (17) depicts a triazine resin obtained from a melamine-butanediol-precondensate, melamine and formaldehyde. Due to the integration of longer linked bridges (here C4 bridges) the resin is more flexible. The structure is still similar to MF-resin and water soluble which makes the use of existing processing technologies of customers possible. It is to be noted that the condensation product is not yet completely hardened (free methylol groups in the product) and that cyclization of multiple triazines may occur. It is to be pointed out that the condensation product (17) is part of a mixture of condensation products and illustrates one of the possible structures.

In another embodiment a condensation product (18) is obtained from melamine, formaldehyde and a precondensate of formula (II) that in turn was obtained from a reaction of melamine, acetoguanamine and butandiol:

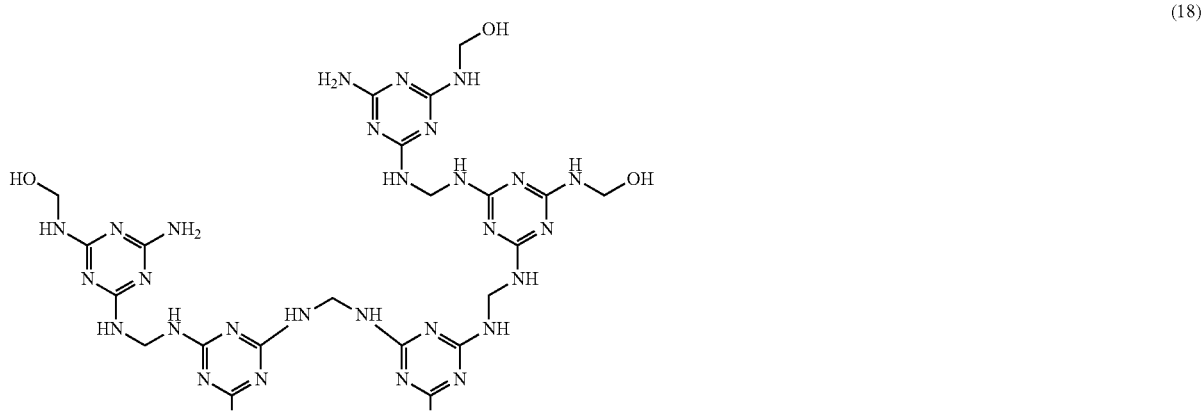

(18)

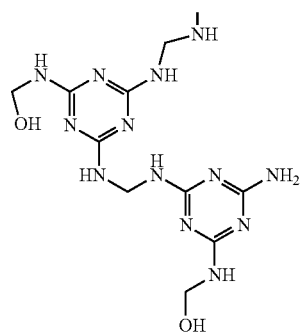
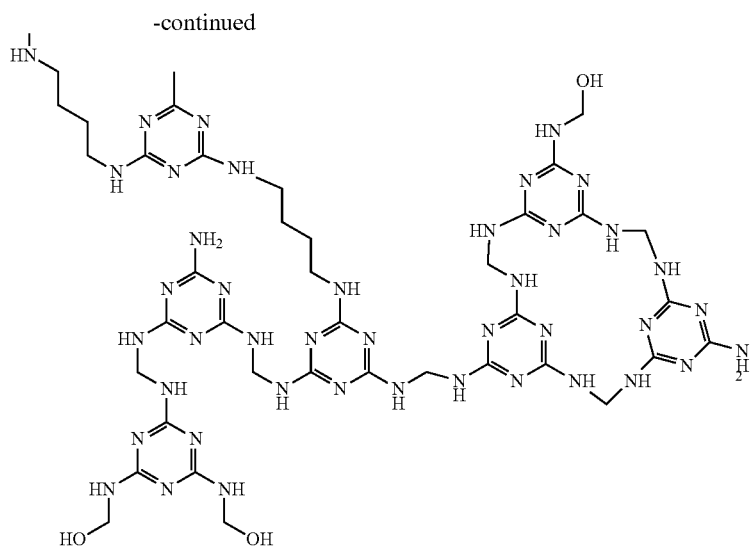
In yet another embodiment condensation product (19) is obtained from melamine, acetoguanamine, formaldehyde and a precondensate of formula (II) that in turn was obtained from a reaction of melamine and butandiol:
(19)
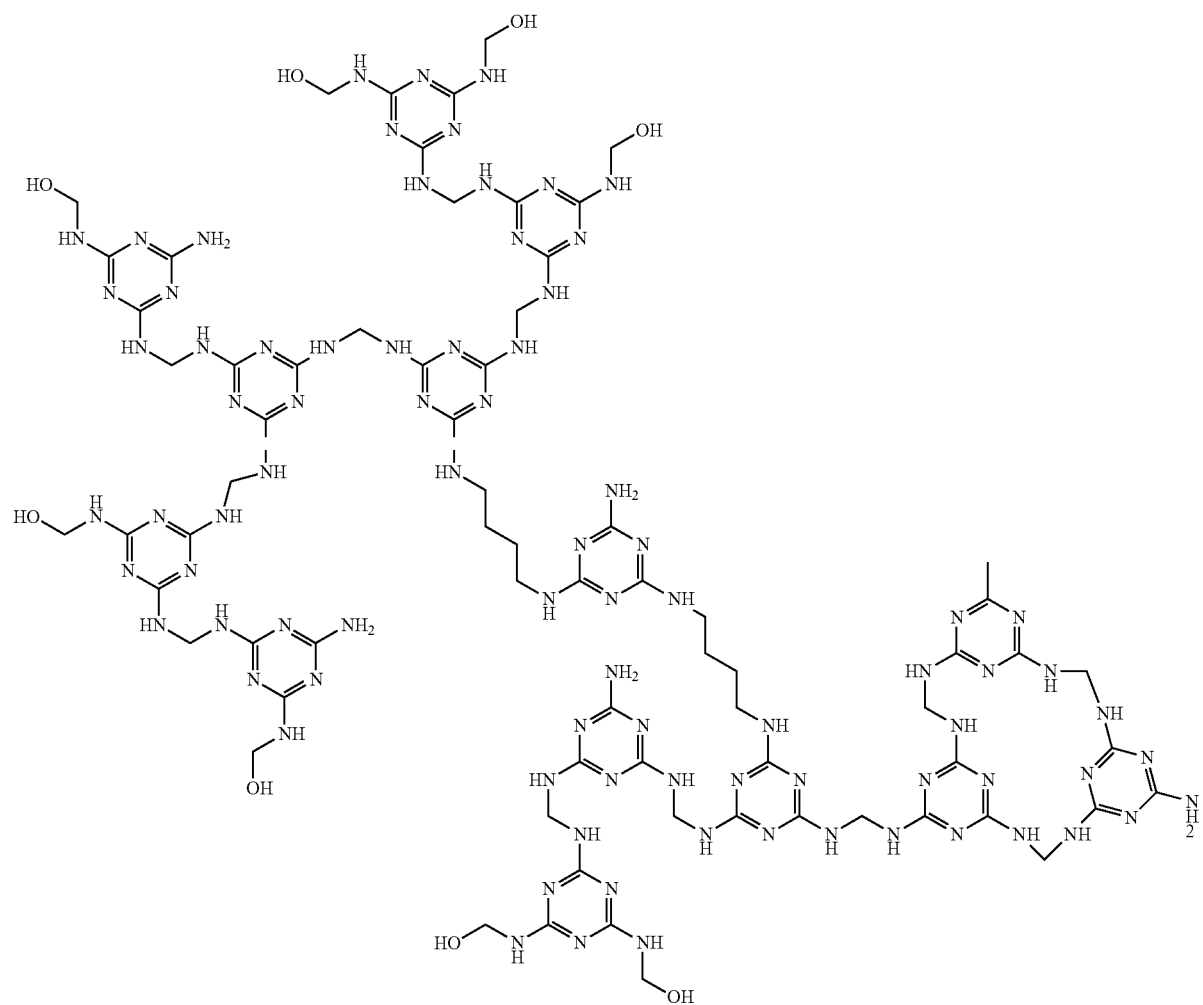

-continued
(20)
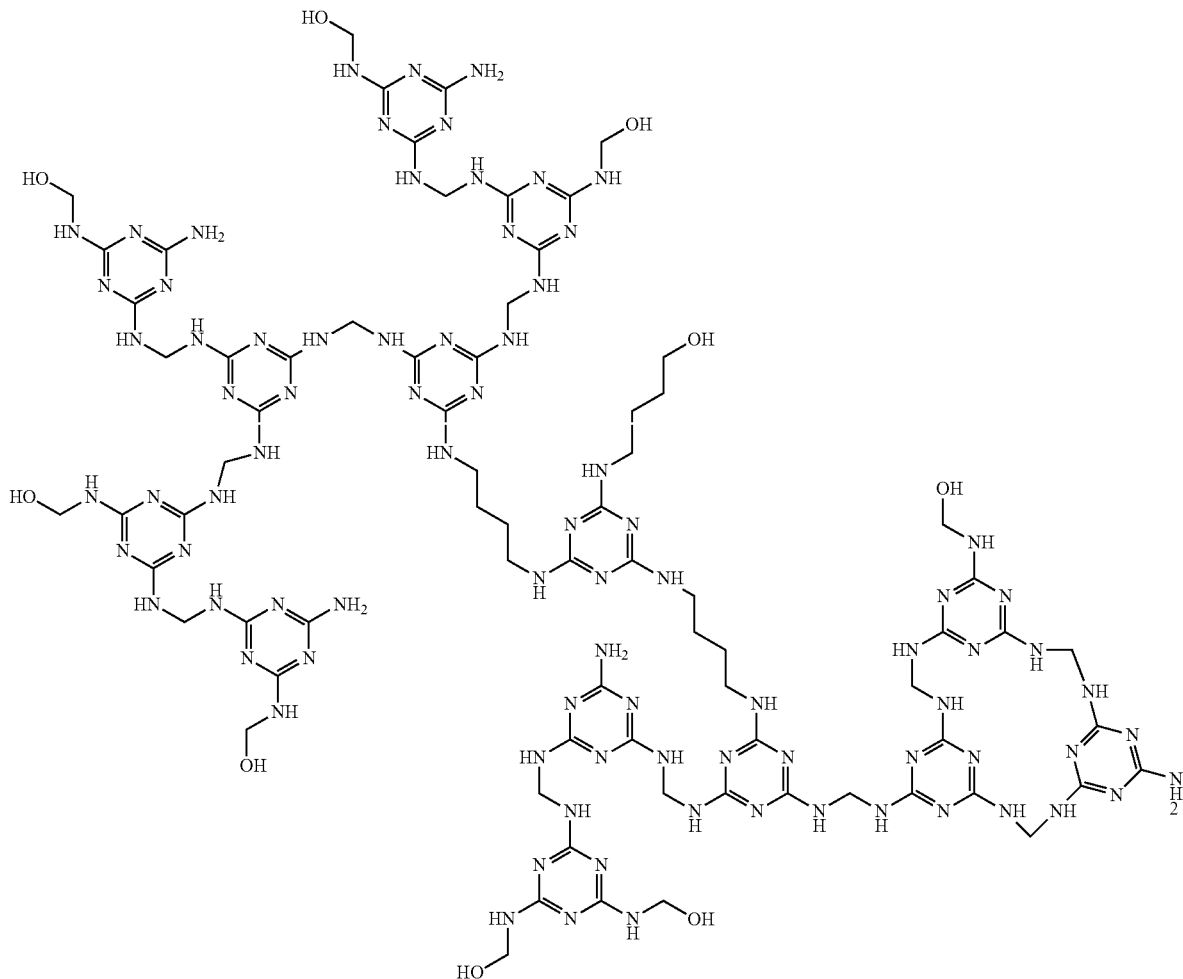
In case of condensation product (20) a precondensate of formulae (II) was used that comprises a free hydroxybutan moiety.
In yet a further embodiment a condensation product (21) is obtained from melamine, formaldehyde and a precondensate of formula (II) that in turn was obtained from a reaction of melamine, benzoguanamine and butandiol:
(21)
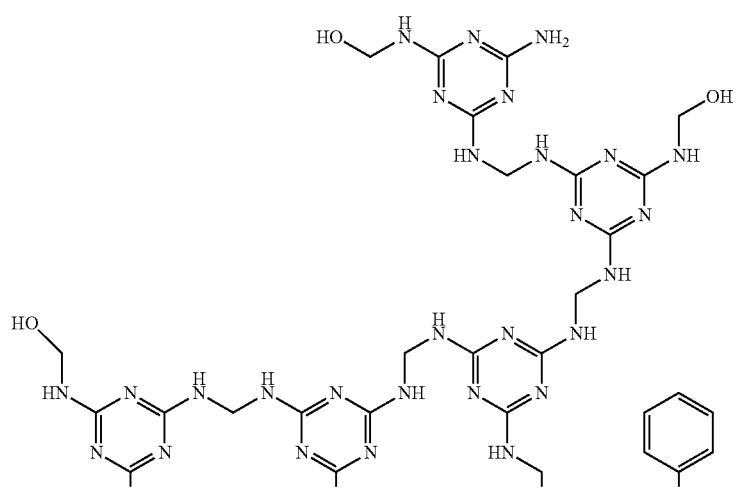

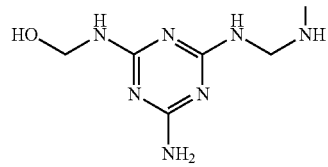
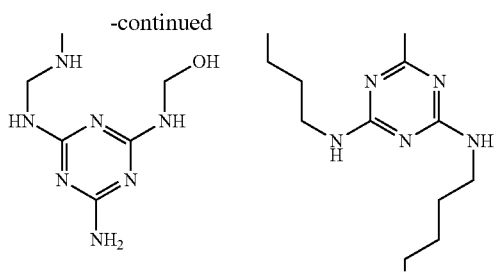
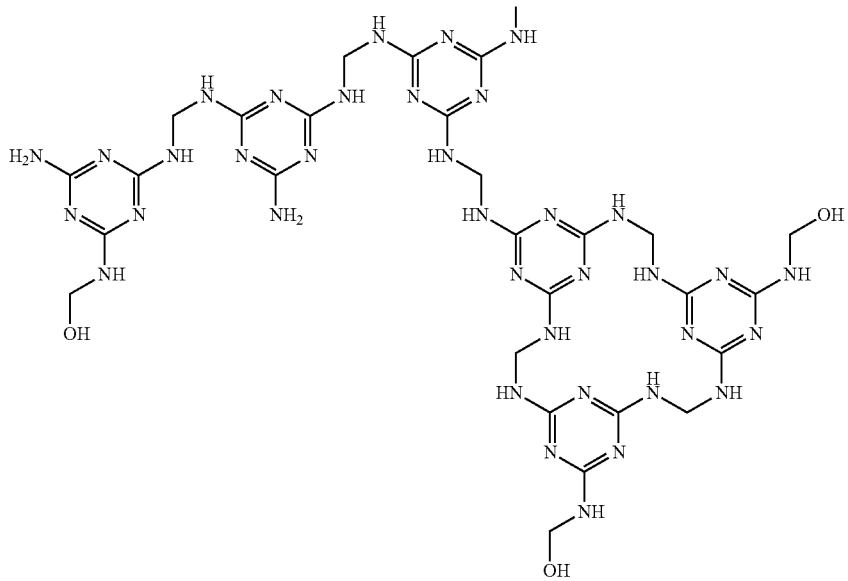
In still another embodiment a condensation product (22) is obtained from melamine, formaldehyde and a precondensate of formula (II) that in turn was obtained from a reaction of melamine and butandiol, wherein the precondensate comprises a pyrrolidin ring due to cyclization of the butandiol moiety:
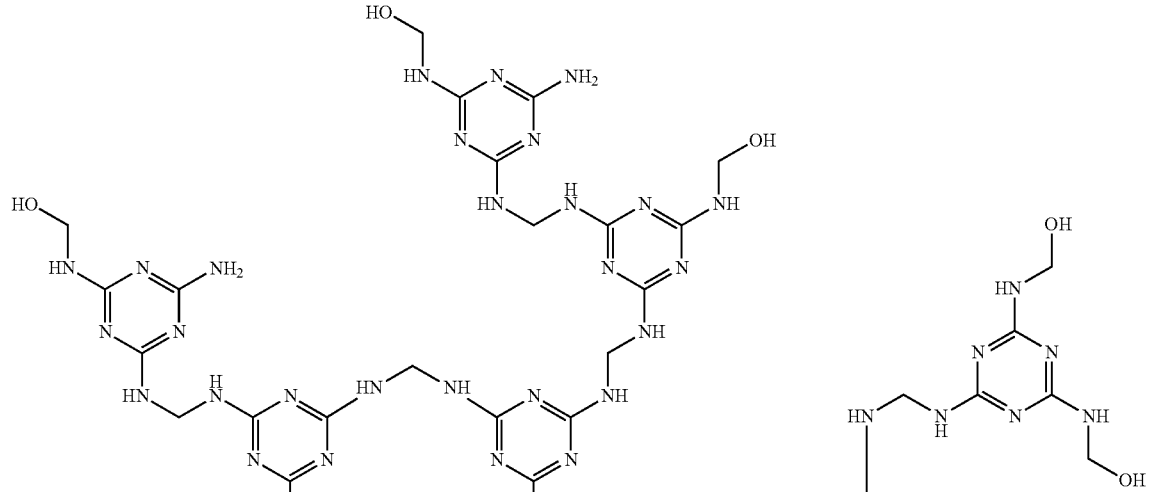
(22)

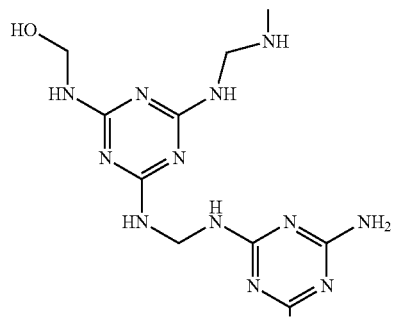
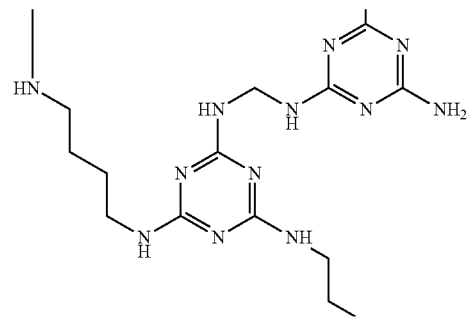
In yet a further embodiment a condensation product (23) is obtained from melamine, formaldehyde and a precondensate of formula (II) that in turn was obtained from a reaction of melamine and pentandiol:
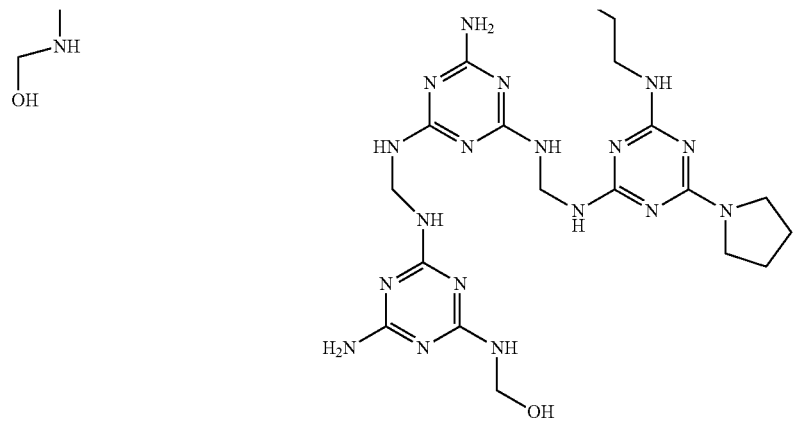
(23)
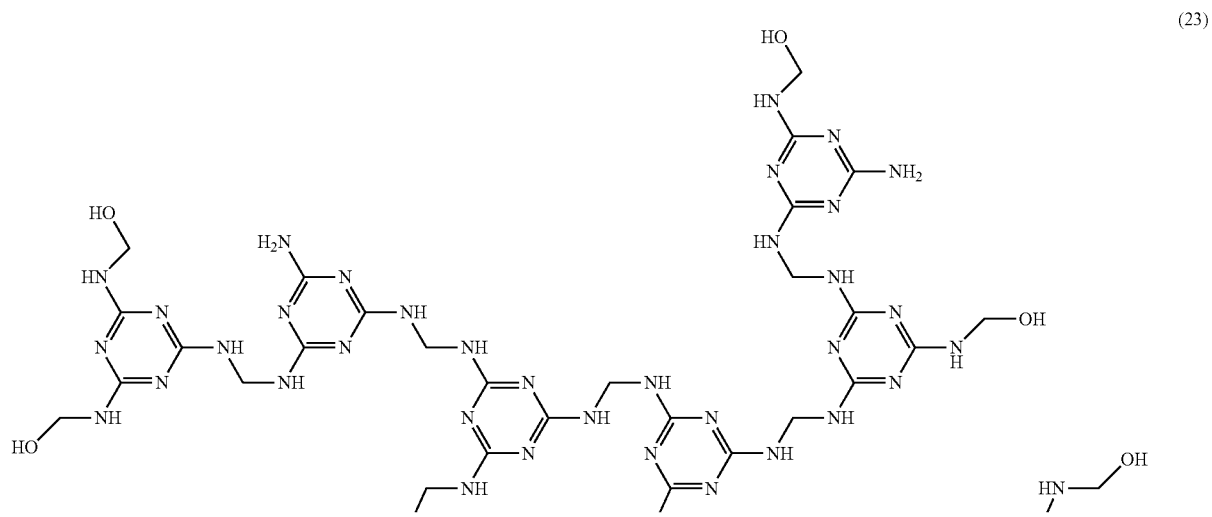

-continued
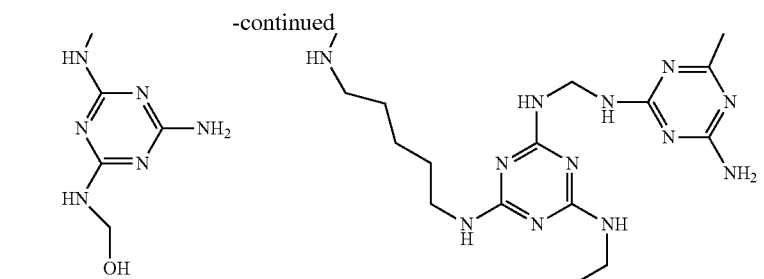
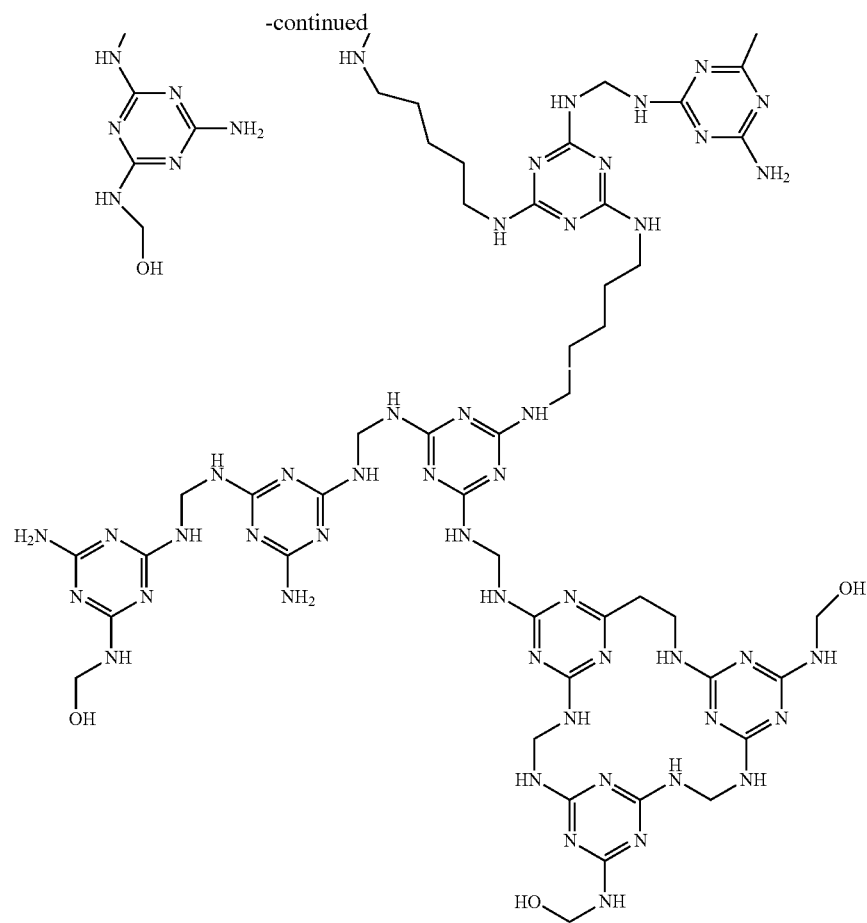
In still a further embodiment a condensation product (24) is obtained from melamine, formaldehyde and a precondensate of formula (II) that in turn was obtained from a reaction of melamine, pentandiol and methanol:
(24)
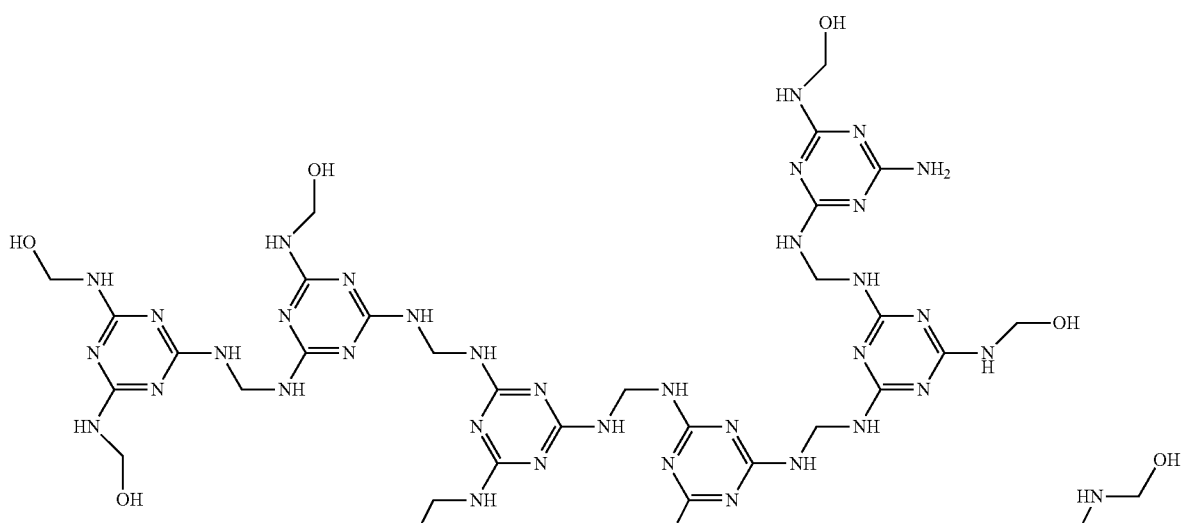

-continued

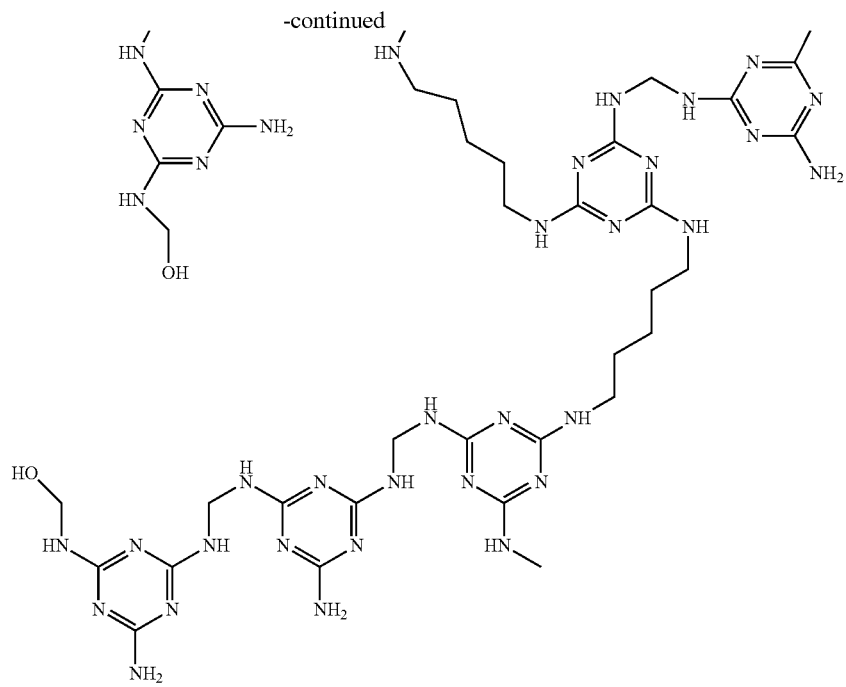

The present triazine-precondensate-aldehyde condensation products are obtained in a method, in particular an aqueous method, comprising the following steps:
providing at least one triazine of general formulae (I),
adding simultaneously or separately at least one triazine precondensate of general formula (II) and at least one aldehyde,
adjusting the pH value of the reaction mixture to a range between 7 and 11, preferably between 8 and 10,
heating the reaction mixture to a temperature between 60° C. and 120° C., preferably 70° C. and 110° C., most preferably 80° C. and 100° C. until a clear solution is obtained,
cooling the reaction mixture until a water tolerance of the mixture of between 1 and 5 (ml/ml), preferably between 2 and 3 (ml/ml) is obtained.

Thus, according the present method a triazine of formulae (I), such as melamine, is reacted with an aldehyde, such as formaldehyde, forming a triazine-aldehyde-condensate, such as melamine-formaldehyde-condensate, and simultaneously or subsequently the triazine precondensate of formulae (II), such as a melamine-diol-precondensate, is added. Due to free NH-moieties the triazine precondensate of formulae (II) can react with the aldehyde via hydroxymethylation and is incorporated into the condensation product. There is no reaction between free OH groups of the diol and the formaldehyde. This provides the unique structures of the present triazine-precondensate-aldehyde condensation products.

The present reaction is preferably carried out in water, in particular in deionized water. It is also possible to add further solvents (as auxiliary solvent) to the reaction mixture, in particular suitable alcohols such as methanol or ethanol.

As mentioned the triazine precondensate of formula (II) may be added separately to the reaction manner. The precondensate of formulae (II) may be added in a time delayed manner, i.e. at any other process step.

It is furthermore preferred if modifiers (as so called flexibility modifiers) are added to the condensate. The modifier can be selected from a group comprising polyols, like ethylenglycol, diethyleneglycol, polyethyleneglycol, trimethylolpropane, sorbitol, dicyandiamide, urea, triethanolamine, caprolactam, sugar and/or o/p-toluene sulphonamide and others. The modifier may be added simultaneously with the precondensate or at a later stage.

In a variant of the present method the pH value is adjusted using an organic or inorganic base, preferably an inorganic base selected from a groups comprising NaOH, $Na_2CO_3$, KOH, $K_2CO_3$, $NH_3$ or alike.

In an embodiment of the present method the reaction mixture is cooled with a cooling rate between 2 and 3 K/min, preferably 2.5 K/min. The cooling may also occur stepwise. For example, in a first step the reaction mixture may be cooled from 98-100° C. to 93° C. with a cooling rate of 2.5 K/min until a water tolerance of 2 ml/ml is obtained followed by further cooling to 25° C. (or room temperature) in a second step.

The present triazine-precondensate-aldehyde condensation product can be used as a cross linker of a coating formulation or a coating such as furniture coating or as impregnation resin for laminate papers or for decor layers of postforming laminates, laminate flooring or 3D laminates, and adhesives such as adhesives for wood based panels. These laminates can be processed as a high pressure laminate (HPL), low pressure laminate (LPL) or a continuous pressure laminate (CPL).

Thus, triazine-precondensate-aldehyde condensation products of the present invention may (after addition of suitable hardeners or linking agents) be used as glues or binders in wood based panels, such as chipboards or particle boards (PB), OSB, MDF, LDF or HDF and plywood.

The use of the rather flexible triazine-precondensate-aldehyde condensation products as coating and/or adhesives allows for an overall improvement and increase of flexibility of the wood based panels obtained thereby. This in turn provides the possibility to produce wood based panels with a rounded or curved surface extending the use of such panels in the furniture industry.

The triazine-precondensate-aldehyde condensation product can be used for example as impregnation resin for laminates whereby the formability of such an impregnated laminate is improved. At the same time the typical melamine-formaldehyde resin properties such as scratch resistance, hardness and acid tolerance are not compromised.

BRIEF DESCRIPTION OF THE DRAWINGS

FIG. 1 shows, schematically, the condensation product of the present invention, as a mixture of MF-precondensates and MD-precondensates.

DESCRIPTION OF THE INVENTION

Further details of the invention will be explained by the means of the following examples.

Example 1

35 g of melamine were mixed with 4 g of melamine butanediol precondensate, 41 g of formaldehyde solution (30%) and 19.18 g of deion. water. After addition of 4 ml 0.1 N NaOH the mixture was heated to 98° C. with a heating rate of 5 K/min. After reaching the clearing point the mixture was cooled to 93° C. with a cooling rate of 2.5 K/min. After reaching a water tolerance of 2.0 (ml/ml) the mixture was cooled to 25° C. with maximum cooling rate. The storage stability of the obtained resin was 10 days.

The water tolerance of a resin is expressed as the ratio of part of water (W1) to one part of resin (W2) or W1/W2, where the resin starts to precipitate.

Example 2

31 g of melamine were mixed with 8 g of melamine butanediol precondensate, 41 g of formaldehyde solution (30%) and 19.18 g of deion. water. After addition of 4 ml 0.1 N NaOH the mixture was heated to 98° C. with a heating rate of 5 K/min. After reaching the clearing point the mixture was cooled to 93° C. with a cooling rate of 2.5 K/min. After reaching a water tolerance of 2.0 (ml/ml) the mixture was cooled to 25° C. with maximum cooling rate. The storage stability of the obtained resin was 3 days.

Example 3

27 g of melamine were mixed with 12 g of melamine butanediol precondensate, 41 g of formaldehyde solution (30%) and 19.18 g of deion. water. After addition of 4 ml 0.1 N NaOH the mixture was heated to 98° C. with a heating rate of 5 K/min. After reaching the clearing point the mixture was cooled to 93° C. with a cooling rate of 2.5 K/min. After reaching a water tolerance of 2.0 (ml/ml) the mixture was cooled to 25° C. with maximum cooling rate. The storage stability of the obtained resin was 1 day.

The invention claimed is:

1. A triazine-precondensate-aldehyde condensation product obtained by reacting a) at least one triazine compound of the general formulae (I)

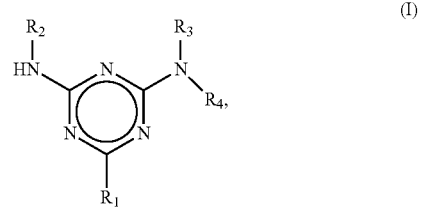

b) at least one aldehyde and c) at least one triazine precondensate of the general formula (II)

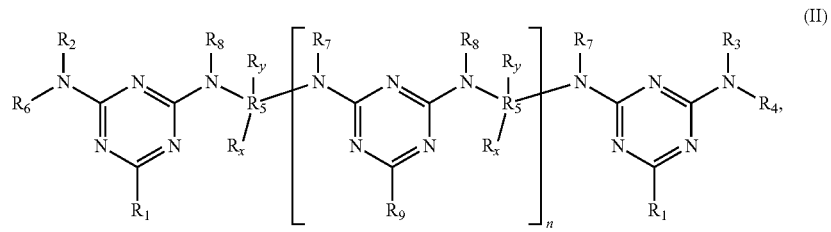

wherein $R_1$ means $Q^1$ or a moiety of the formula $R_3$—N—$R_4$ connected with the nitrogen atom to the respective triazine ring of the structure of formula (I) or (II), $R_9$ means $Q^1$ or a moiety of the formula $R_7$—N—$R_8$ connected with the nitrogen atom to the triazine ring of the structure of formula (II), $R_2$, $R_3$, $R_4$ and $R_6$ mean independently from each other H, $Q^1$ or

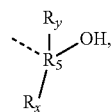

$R_7$ and $R_8$ mean independently from each other H, $Q^1$,

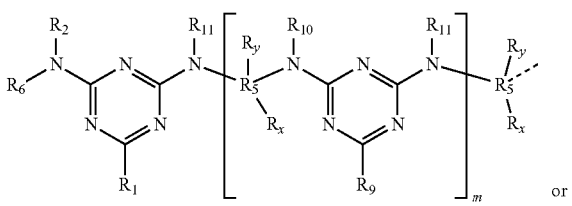

or

-continued

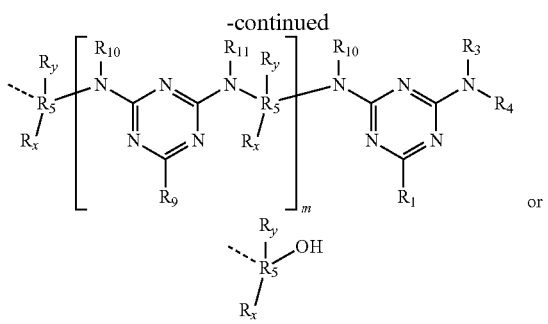

$R_{10}$ and $R_{11}$ mean independently from each other $R_7$ or $R_8$;

$R_5$ means linear or branched $C_2$-$C_{20}$-alkyl that can be interrupted by one or more oxygen atoms, sulphur atoms, substituted or non-substituted nitrogen atoms $R_x$, $R_y$, mean independently from each other H, OH, $Q^1$, —[$C_1$-$C_{18}$]—OH or

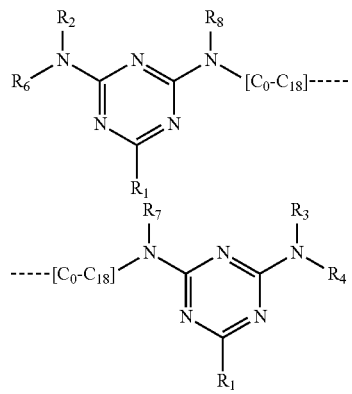

wherein $Q^1$ means linear or branched $C_1$-$C_{20}$-alkyl, linear or branched $C_2$-$C_{20}$-alkenyl, linear or branched $C_2$-$C_{20}$-alkinyl, $C_3$-$C_{10}$-cycloalkyl, $C_5$-$C_7$-cycloalkenyl, which in each case can be interrupted by one or more oxygen atoms, sulphur atoms, substituted or non-substituted nitrogen atoms and/or by one or more groups of the type —C(O)O—, —OC(O)—, —C(O)—, —NHC(O)O—, —OC(O)NH— and/or —OC(O)O—; and wherein n=0-10;

m=0-8;

or mixtures thereof, and wherein the molar ratio of the at least one aldehyde to the at least one triazine of general formulae (I), and the at least one precondensate of the general formulae (II) is in each case in a range between 0.4:1 and 3:1.

2. The condensation product according to claim 1, wherein $Q^1$ is a linear or branched $C_1$-$C_{12}$-alkyl, $C_3$-$C_7$-cycloalkyl and linear or branched $C_2$-$C_{12}$-alkenyl.

3. The condensation product according to claim 1, wherein $Q^1$ is a linear or branched $C_1$-$C_6$ alkyl.

4. The condensation product according to claim 1, wherein the moieties $R_2$, $R_3$, $R_4$, $R_6$, $R_7$ and $R_8$ are H or a $C_1$-$C_6$ alkyl comprising in one or more cases at least one OH substituent.

5. The condensation product according to claim 1, wherein the moieties $R_2$, $R_3$, $R_4$, $R_6$, $R_7$ and $R_8$ are in each case H and $R_5$ is a $C_2$-$C_6$ alkyl.

6. The condensation product according to claim 1, wherein the at least one triazine of general formulae (I) is selected from a group comprising melamine, acetoguanamine, benzoguanamine or alkylated melamine and optionally that at least one further amino compound is added.

7. The condensation product according to claim 1, wherein the at least one aldehyde is formaldehyde.

8. The condensation product according to claim 1, comprising an average molar mass M between 400 and 5000 g/mol.

9. The condensation product according to claim 1, comprising a storage stability between 1 and 40 days.

10. A method for obtaining a condensation product according to claim 1 comprising:
    providing at least one triazine of general formulae (I),
    adding simultaneously or separately at least one precondensate of general formula (II) and at least one aldehyde,
    adjusting the pH value of the reaction mixture to a range between 7 and 11,
    heating the reaction mixture to a temperature between 60° C. and 120° C. until a clear solution is obtained,
    cooling the reaction mixture until a water tolerance of the mixture of between 1 and 5 (ml/ml) is obtained.

11. The method according to claim 10, wherein the reaction is carried out in water.

12. The method according to claim 10, wherein the pH value is adjusted using an organic or inorganic base.

13. Wood based panels comprising a condensation product according to claim 1.

14. The condensation product according to claim 6, wherein the at least one further amino compound comprises urea or a derivative thereof.

15. The condensation product according to claim 1, wherein n=1-5.

16. The condensation product according to claim 1, wherein m=1-5.

17. The condensation product according to claim 3, wherein $Q^1$ is a linear or branched $C_2$, $C_3$, or $C_4$ alkyl.

18. The condensation product according to claim 8, wherein M is between 500 and 3000 g/mol.

19. The wood based panels according to claim 13, wherein the wood based panels comprise particle board, OSB, MDF, LDF, HDF, or plywood.

* * * * *